United States Patent
Buchanan (10) Patent No.: US 12,119,113 B2
(45) Date of Patent: Oct. 15, 2024

(54) APPARATUS, METHOD, AND PROGRAM PRODUCT FOR REMOTE DENTISTRY

(71) Applicant: Julie Buchanan, St. George, UT (US)

(72) Inventor: Julie Buchanan, St. George, UT (US)

(73) Assignee: Julie Buchanan, St. George, UT (US)

( * ) Notice: Subject to any disclaimer, the term of this patent is extended or adjusted under 35 U.S.C. 154(b) by 768 days.

(21) Appl. No.: 16/442,875

(22) Filed: Jun. 17, 2019

(65) Prior Publication Data
US 2019/0385742 A1  Dec. 19, 2019

Related U.S. Application Data

(60) Provisional application No. 62/685,432, filed on Jun. 15, 2018.

(51) Int. Cl.
*G16H 50/20* (2018.01)
*A61B 1/24* (2006.01)
(Continued)

(52) U.S. Cl.
CPC ........... *G16H 50/20* (2018.01); *A61B 5/0035* (2013.01); *A61B 5/0088* (2013.01); *A61B 6/51* (2024.01);
(Continued)

(58) Field of Classification Search
CPC ........ G16H 50/20; G16H 20/10; G16H 30/40; G16H 20/00; G16H 40/67; A61B 5/0035; A61B 5/0088; A61B 6/14; A61B 1/24; A61B 5/0002; A61B 6/563; A61B 6/566; G06T 7/0012; G06T 2207/10016; G06T 2207/10116; G06T 2207/30036
(Continued)

(56) References Cited

U.S. PATENT DOCUMENTS 6,893,259 B1 * 5/2005 Reizenson ......... A61C 17/0211
                                                        433/29
7,156,655 B2   1/2007 Sachdeva
                (Continued)

FOREIGN PATENT DOCUMENTS

WO   2014172761 A2   10/2014
WO   2015192138 A1   12/2015
WO   2017105602 A1    6/2017

OTHER PUBLICATIONS

A. Shailee, F., Sogi, G. M., Sharma, K. R., & Vinay, B. (2013). Teledentistry the future of dental practice. Indian Journal of Dental Advancements, 5(2), 1195(5). (Year: 2013).*

*Primary Examiner* — Amber A Misiaszek
(74) *Attorney, Agent, or Firm* — Kunzler Bean & Adamson (57) ABSTRACT

An apparatus, method, system, and program product are disclosed for remote dentistry. One apparatus includes an information reception module of a diagnostic processing device that receives digital dental information. The apparatus includes an issue determination module that determines a dental related issue based on the digital dental information. The apparatus includes a treatment module that transmits treatment information for the dental related issue from the diagnostic processing device. At least a portion of the information reception module, the issue determination module, and the treatment module includes one or more of hardware and executable code. The executable code may be stored on one or more computer readable storage media.

3 Claims, 5 Drawing Sheets

(51) Int. Cl.
*A61B 5/00* (2006.01)
*A61B 6/51* (2024.01)
*G06T 7/00* (2017.01)
*G16H 20/10* (2018.01)
*G16H 30/40* (2018.01)

(52) U.S. Cl.
CPC ........... *G06T 7/0012* (2013.01); *G16H 20/10* (2018.01); *G16H 30/40* (2018.01); *A61B 1/24* (2013.01); *G06T 2207/10016* (2013.01); *G06T 2207/10116* (2013.01); *G06T 2207/30036* (2013.01)

(58) Field of Classification Search
USPC .......................................................... 705/2–3
See application file for complete search history.

(56) References Cited

U.S. PATENT DOCUMENTS

| | | | |
|---|---|---|---|
| 7,523,044 B2 | 4/2009 | Rosenblood | |
| 8,751,039 B1 * | 6/2014 | Macoviak | G16H 40/63 700/244 |
| 9,202,253 B2 * | 12/2015 | Macoviak | G16H 40/20 |
| 2003/0078806 A1 | 4/2003 | Kudryk | |
| 2004/0118427 A1 * | 6/2004 | Palfy | A61C 17/036 250/493.1 |
| 2005/0027567 A1 * | 2/2005 | Taha | G16H 10/20 705/2 |
| 2005/0186533 A1 * | 8/2005 | Cohen | A61G 15/14 433/108 |
| 2007/0128574 A1 * | 6/2007 | Kuo | G16H 30/20 433/24 |
| 2009/0259492 A1 | 10/2009 | Cossman | |
| 2011/0010200 A1 | 1/2011 | Firozvi | |
| 2011/0028884 A1 | 2/2011 | Theodore Coroneo | |
| 2011/0288884 A1 | 11/2011 | Algoo | |
| 2012/0046668 A1 * | 2/2012 | Gantes | A61B 34/25 606/130 |
| 2012/0191470 A1 * | 7/2012 | Winston | G16H 10/20 705/2 |
| 2013/0025339 A1 | 1/2013 | Costa et al. | |
| 2013/0035955 A1 | 2/2013 | Torres | |
| 2013/0138458 A1 | 5/2013 | Lorsch | |
| 2013/0253339 A1 | 9/2013 | Reyes | |
| 2013/0310725 A1 * | 11/2013 | Jerrells | A61F 13/0246 602/43 |
| 2013/0310726 A1 * | 11/2013 | Miller | G16H 40/63 717/173 |
| 2013/0317838 A1 | 11/2013 | Schoenberg | |
| 2014/0039912 A1 | 2/2014 | Turinas | |
| 2014/0052463 A1 | 2/2014 | Cashman | |
| 2014/0058755 A1 | 2/2014 | Macoviak | |
| 2014/0164022 A1 | 6/2014 | Reed | |
| 2014/0276375 A1 * | 9/2014 | Minkus | A61M 1/159 705/2 |
| 2014/0296871 A1 * | 10/2014 | Chen | A61B 34/30 606/130 |
| 2015/0278453 A1 | 10/2015 | Joao | |
| 2016/0246936 A1 | 8/2016 | Kahn | |
| 2016/0335408 A1 * | 11/2016 | Cosse | G16H 10/60 |
| 2017/0032092 A1 | 2/2017 | Mink | |
| 2017/0083676 A1 | 3/2017 | Sigler | |
| 2017/0329922 A1 | 11/2017 | Eberting | |
| 2018/0064326 A1 | 3/2018 | Patrick | |

\* cited by examiner

APPARATUS, METHOD, AND PROGRAM PRODUCT FOR REMOTE DENTISTRY

CROSS-REFERENCE TO RELATED APPLICATIONS

This application claims priority to U.S. Patent Application Ser. No. 62/685,432 entitled "APPARATUS, METHOD, AND PROGRAM PRODUCT FOR REMOTE DENTISTRY" and filed on Jun. 15, 2018 for Julie Buchanan, which is incorporated herein by reference in its entirety.

FIELD

The subject matter disclosed herein relates to dentistry and more particularly relates to apparatuses, methods, and program products for remote dentistry.

BACKGROUND

Dental examinations are traditionally initiated by a patient scheduling an appointment with a dental office. The patient then visits the dental office for their scheduled appointment.

BRIEF SUMMARY

An apparatus for remote dentistry is disclosed. A method and computer program product also perform the functions of the apparatus. In one embodiment, an apparatus includes an information reception module of a diagnostic processing device that receives digital dental information. The apparatus, in a further embodiment, includes an issue determination module that determines a dental related issue based on the digital dental information. In various embodiments, the apparatus includes a treatment module that transmits treatment information for the dental related issue from the diagnostic processing device. In certain embodiments, at least a portion of the information reception module, the issue determination module, and the treatment module includes one or more of hardware and executable code. The executable code may be stored on one or more computer readable storage media.

A method for remote dentistry, in one embodiment, includes receiving digital dental information at a diagnostic processing device. In various embodiments, the method includes determining a dental related issue based on the digital dental information. The method includes, in one embodiment, transmitting treatment information for the dental related issue from the diagnostic processing device.

In one embodiment, a computer program product for remote dentistry includes a non-transitory computer readable storage medium having program instructions embodied therewith. The program instructions, in some embodiments, are executable by a processor to cause the processor to receive digital dental information at a diagnostic processing device. The program instructions, in one embodiment, are executable by a processor to cause the processor to determine a dental related issue based on the digital dental information. In a further embodiment, the program instructions are executable by a processor to cause the processor to transmit treatment information for the dental related issue from the diagnostic processing device.

BRIEF DESCRIPTION OF THE DRAWINGS

In order that the advantages of the embodiments of the invention will be readily understood, a more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory ("RAM"), a read-only memory ("ROM"), an erasable programmable read-only memory ("EPROM" or Flash memory), a static random access memory ("SRAM"), a portable compact disc read-only memory ("CD-ROM"), a digital versatile disk ("DVD"), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture ("ISA") instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider). In some embodiments, electronic circuitry including, for example, programmable logic circuitry, field-programmable gate arrays ("FPGA"), or programmable logic arrays ("PLA") may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program instructions may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

The schematic flowchart diagrams and/or schematic block diagrams in the Figures illustrate the architecture, functionality, and operation of possible implementations. It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Although various arrow types and line types may be employed in the flowchart and/or block diagrams, they are understood not to limit the scope of the corresponding embodiments. Indeed, some arrows or other connectors may be used to indicate only an exemplary logical flow of the depicted embodiment.

The description of elements in each figure may refer to elements of proceeding figures. Like numbers refer to like elements in all figures, including alternate embodiments of like elements.

Figure 1:
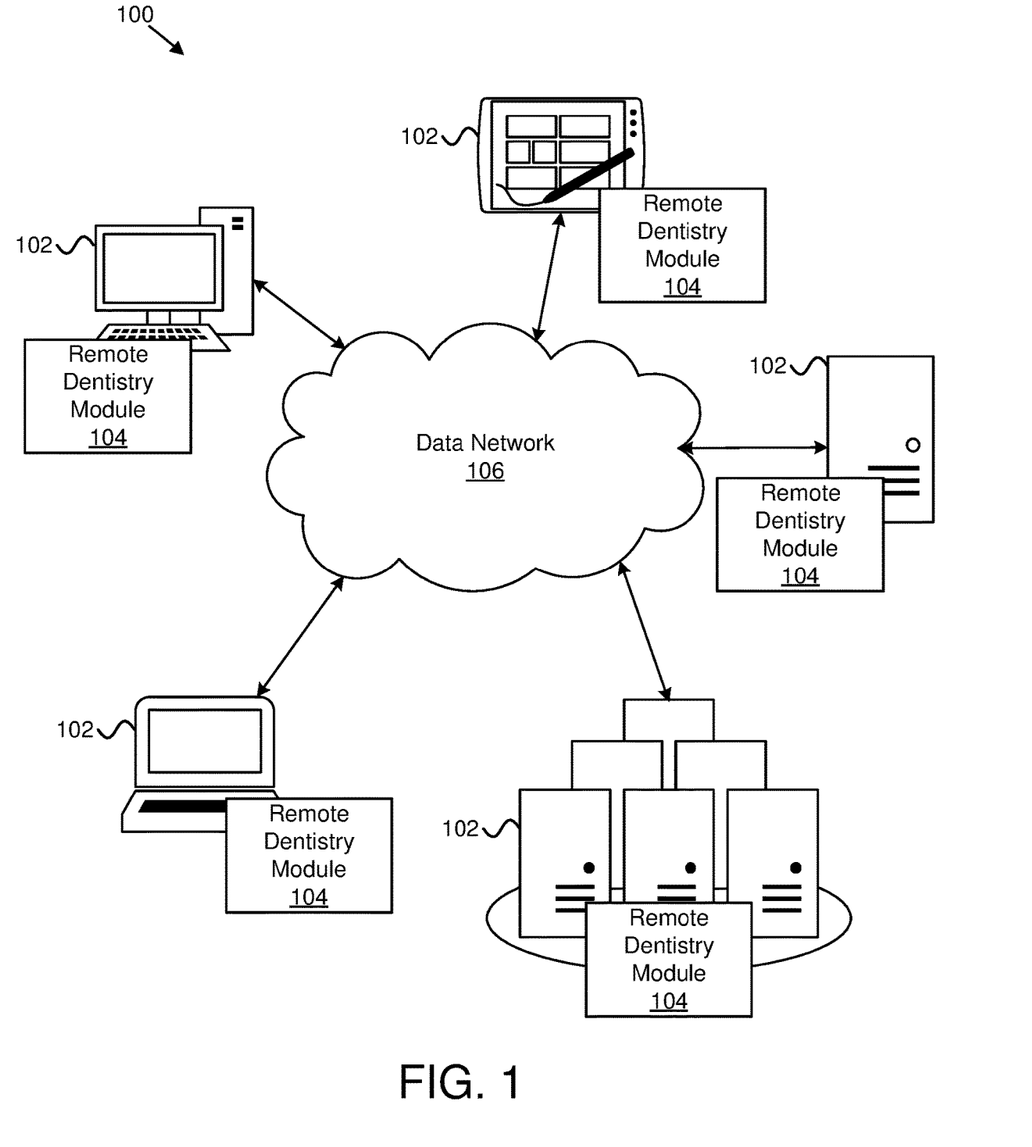
FIG. 1 is a schematic block diagram illustrating one embodiment of a system for remote dentistry.

FIG. 1 depicts one embodiment of a system 100 for remote dentistry. In one embodiment, the system 100 includes information handling devices 102, remote dentistry modules 104, and data networks 106. Even though a particular number of information handling devices 102, remote dentistry modules 104, and data networks 106 are depicted in the system 100 of FIG. 1, one of skill in the art will recognize that any number or configuration of information handling devices 102, remote dentistry modules 104, and data networks 106 may be present in the system 100.

The information handling devices 102, in certain embodiments, include computing devices, such as desktop computers, laptop computers, tablet computers, smart phones, smart televisions, or the like. The information handling devices 102 may also include servers, such as web servers, application servers, file servers, media servers, email servers, cloud servers, backup servers, virtual servers, or the like. The information handling devices 102 may be located in geographically remote locations, in the same geographic location, or some combination of both.

In one embodiment, the remote dentistry module 104 receives digital dental information at a diagnostic processing device. In various embodiments, the remote dentistry module 104 determines a dental related issue based on the digital dental information. In one embodiment, remote dentistry module 104 transmits treatment information for the dental related issue from the diagnostic processing device. In this manner, the remote dentistry module 104 may facilitate remote dentistry. Ultimately, this may facilitate providing faster dental services, dental services to remote locations, more accurate and/or precise dental services, and so forth.

In certain embodiments, as described below with reference to FIG. 3, the remote dentistry module 104 includes multiple modules that perform the operations of the remote dentistry module 104.

The data network 106, in one embodiment, includes a digital communication network that transmits digital communications. The data network 106 may include a wireless network, such as a wireless cellular network, a local wireless network, such as a Wi-Fi network, a Bluetooth® network, a near-field communication ("NFC") network, an ad hoc network, and/or the like. The data network 106 may include a wide area network ("WAN"), a storage area network ("SAN"), a local area network ("LAN"), an optical fiber network, the internet, or other digital communication network. The data network 106 may include two or more networks. The data network 106 may include one or more servers, routers, switches, and/or other networking equipment. The data network 106 may also include computer readable storage media, such as a hard disk drive, an optical drive, non-volatile memory, RAM, or the like.

Figure 2:
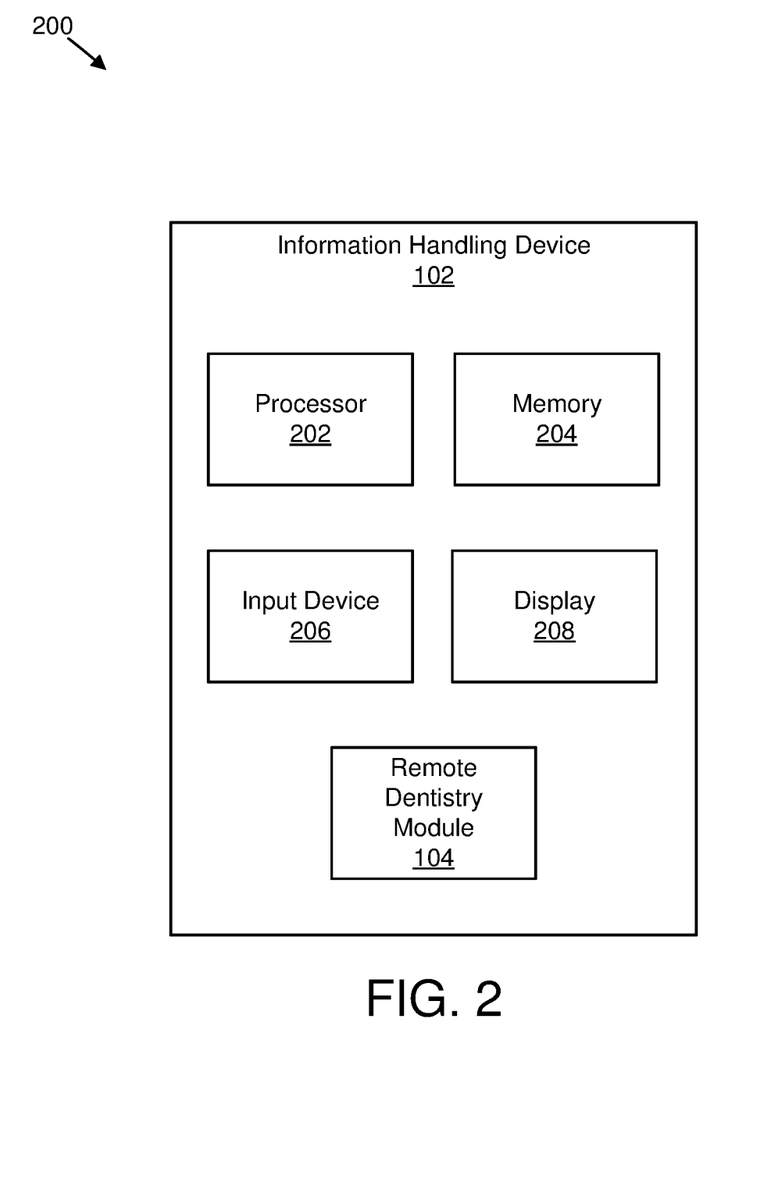
FIG. 2 is a schematic block diagram illustrating one embodiment of an apparatus for remote dentistry.

FIG. 2 depicts one embodiment of an apparatus 200 that may be used for remote dentistry. The apparatus 200 includes one embodiment of the information handling device 102. Furthermore, the information handling device 102 may include a processor 202, a memory 204, an input device 206, a display 208, and the remote dentistry module 104. In some embodiments, the input device 206 and the display 208 are combined into a single device, such as a touchscreen. In certain embodiments, the information handling device 102 may not include any input device 206 and/or display 208. In various embodiments, the information handling device 102 may include one or more of the processor 202, and the memory 204, and may not include the input device 206 and/or the display 208.

The processor 202, in one embodiment, may include any known controller capable of executing computer-readable instructions and/or capable of performing logical operations. For example, the processor 202 may be a microcontroller, a microprocessor, a central processing unit ("CPU"), a graphics processing unit ("GPU"), an auxiliary processing unit, a field programmable gate array ("FPGA"), or similar programmable controller. In some embodiments, the processor 202 executes instructions stored in the memory 204 to perform the methods and routines described herein. In certain embodiments, the processor 202 may be used to: receive digital dental information at a diagnostic processing device; determine a dental related issue based on the digital dental information; and/or transmit treatment information for the dental related issue from the diagnostic processing device. The processor 202 is communicatively coupled to the memory 204, the input device 206, and the display 208.

The memory 204, in one embodiment, is a computer readable storage medium. In some embodiments, the memory 204 includes volatile computer storage media. For example, the memory 204 may include a RAM, including dynamic RAM ("DRAM"), synchronous dynamic RAM ("SDRAM"), and/or static RAM ("SRAM"). In some embodiments, the memory 204 includes non-volatile computer storage media. For example, the memory 204 may include a hard disk drive, a flash memory, or any other suitable non-volatile computer storage device. In some embodiments, the memory 204 includes both volatile and non-volatile computer storage media. In some embodiments, the memory 204 also stores program code and related data, such as an operating system or other controller algorithms operating on the information handling device 102.

The input device 206, in one embodiment, may include any known computer input device including a touch panel, a button, a keyboard, a stylus, a microphone, or the like. In some embodiments, the input device 206 may be integrated with the display 208, for example, as a touchscreen or similar touch-sensitive display. In some embodiments, the input device 206 includes a touchscreen such that text may be input using a virtual keyboard displayed on the touchscreen and/or by handwriting on the touchscreen. In some embodiments, the input device 206 includes two or more different devices, such as a keyboard and a touch panel.

The display 208, in one embodiment, may include any known electronically controllable display or display device. The display 208 may be designed to output visual, audible, and/or haptic signals. In some embodiments, the display 208 includes an electronic display capable of outputting visual data to a user. For example, the display 208 may include, but is not limited to, an LCD display, an LED display, an OLED display, a projector, or similar display device capable of outputting images, text, or the like to a user. As another, non-limiting, example, the display 208 may include a wearable display such as a smart watch, smart glasses, a heads-up display, or the like. Further, the display 208 may be a component of a smart phone, a personal digital assistant, a television, a table computer, a notebook (laptop) computer, a personal computer, a vehicle dashboard, or the like.

In certain embodiments, the display 208 includes one or more speakers for producing sound. For example, the display 208 may produce an audible alert or notification (e.g., a beep or chime). In some embodiments, the display 208 includes one or more haptic devices for producing vibrations, motion, or other haptic feedback. In some embodiments, all or portions of the display 208 may be integrated with the input device 206. For example, the input device 206 and display 208 may form a touchscreen or similar touch-sensitive display. In other embodiments, the display 208 may be located near the input device 206.

In some embodiments, the remote dentistry module 104 may be used to receive digital dental information at a diagnostic processing device, determine a dental related issue based on the digital dental information, and transmit treatment information for the dental related issue from the diagnostic processing device.

Figure 3:
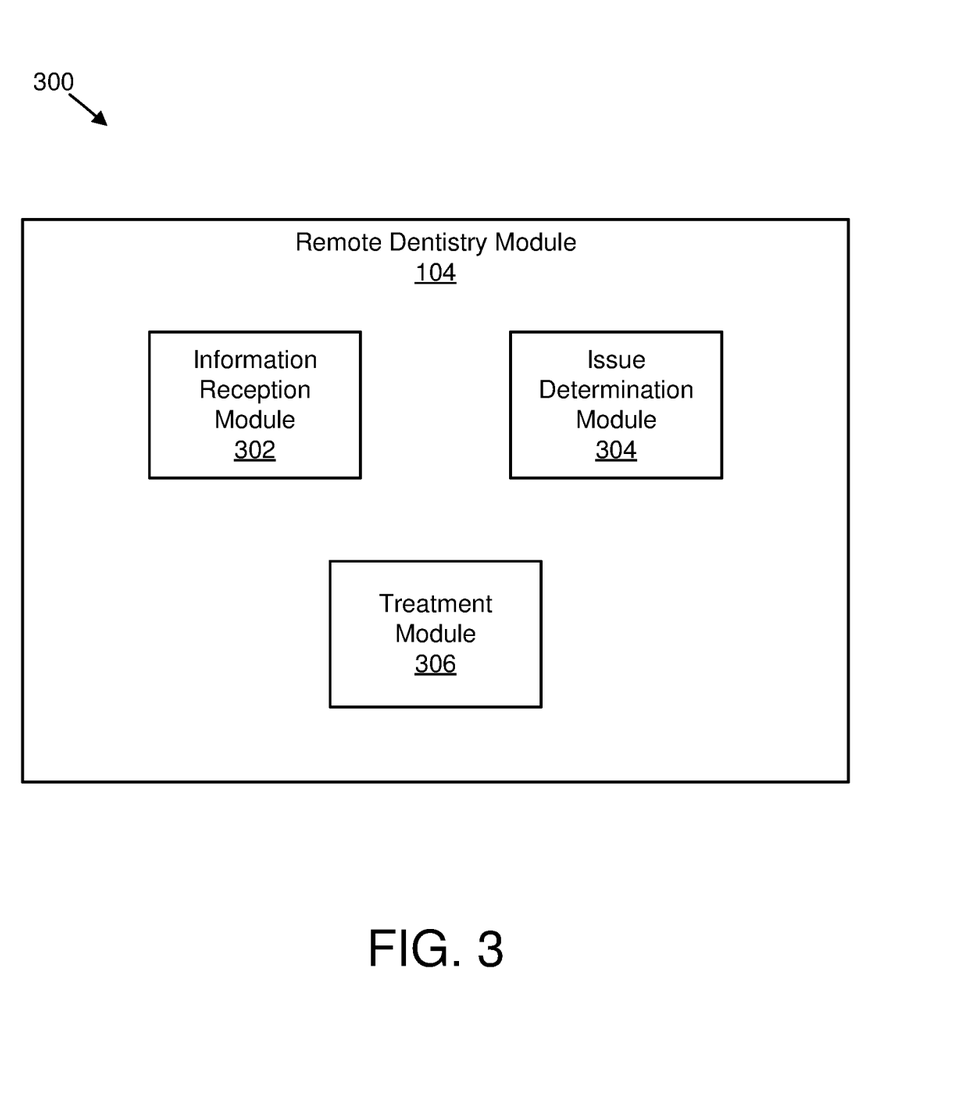
FIG. 3 is a schematic block diagram illustrating one embodiment of a module for remote dentistry.

FIG. 3 is a schematic block diagram illustrating one embodiment of a module 300 for remote dentistry. In one embodiment, the module 300 includes an embodiment of a remote dentistry module 104. The remote dentistry module 104, in various embodiments, includes one or more of an information reception module 302, an issue determination module 304, and a treatment module 306, which are described in more detail below.

In one embodiment, the information reception module 302 receives digital dental information at a diagnostic processing device. The digital dental information may be any type of dental information that has been converted into a digital format. In the digital format, the diagnostic processing device is able to use various analytical techniques to determine a diagnosis based on the digital dental information. In certain embodiments, the digital dental information includes an image of a tooth, a face, a mouth, or some combination thereof. In various embodiments, the image includes an x-ray, a picture, a video, or some combination thereof. The diagnostic processing device may be any suitable device that can receive and/or analyze the digital dental information. For example, the diagnostic processing device may be a combination of specialized hardware and/or software that receives and/or analyzes the digital dental information. The specialized hardware may include programmed logic devices, artificial intelligence based hardware, and so forth.

The issue determination module 304, in one embodiment, determines a dental related issue based on the digital dental information. In some embodiments, the issue determination module 304 digitally analyzes the digital dental information and determines the dental related issue as a result of digitally analyzing the digital dental information.

The treatment module 306, in one embodiment, transmits treatment information for the dental related issue from the diagnostic processing device. In certain embodiments, the treatment module 306 transmits a prescription. In various embodiments, the treatment module 306 transmits instructions to treat the dental related issue. In some embodiments, the treatment module 306 performs the treatment on a patient by verbally instructing the patient on how to perform the treatment. In certain embodiments, the treatment module 306 transmits the treatment information to a machine that performs the treatment on a patent.

Figure 4:
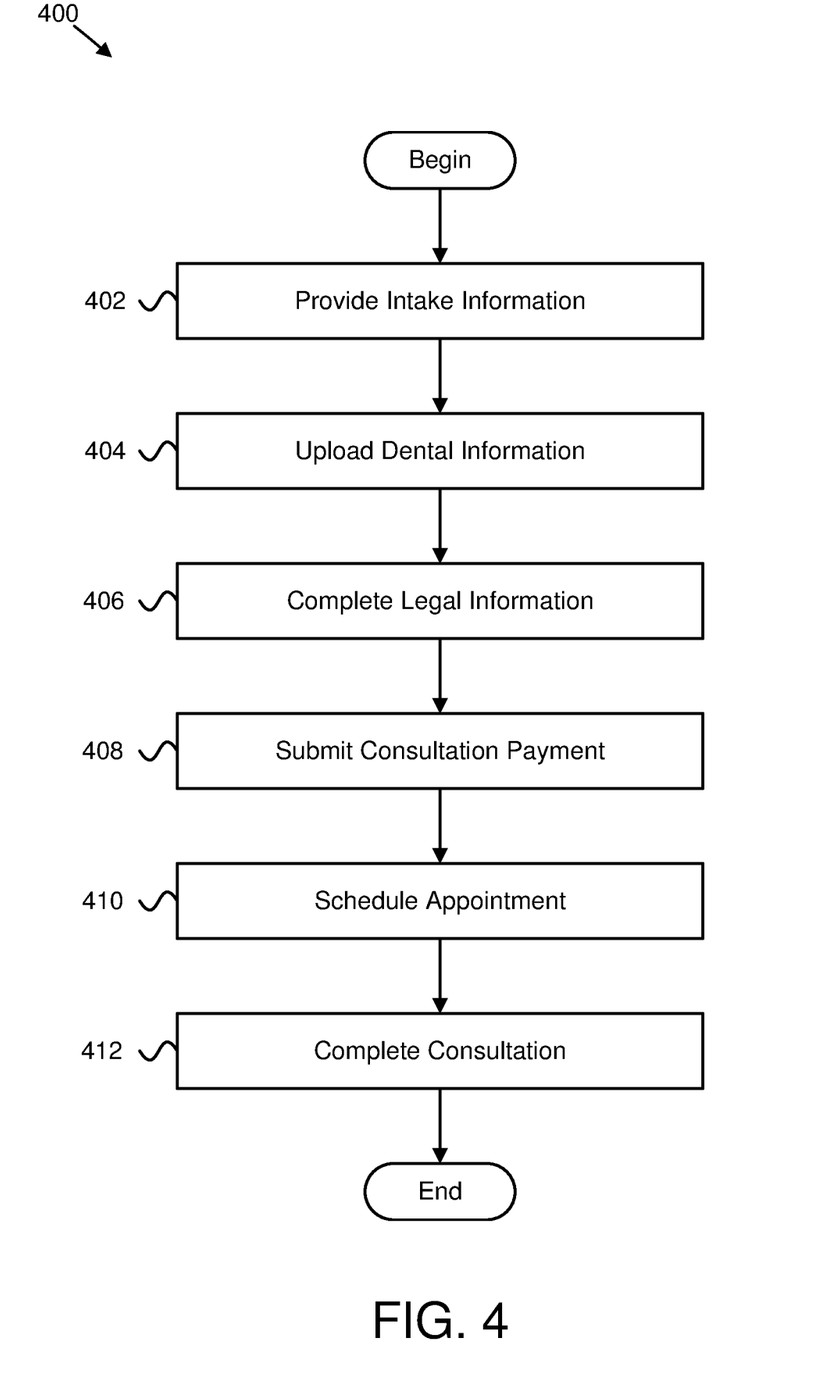
FIG. 4 is a schematic flow chart diagram illustrating one embodiment of a method for remote dentistry.

FIG. 4 is a schematic flow chart diagram illustrating one embodiment of a method 400 for remote dentistry. In some embodiments, the method 400 is performed by an apparatus, such as the information handling device 102. In certain embodiments, the method 400 may be performed by a processor executing program code, for example, a microcontroller, a microprocessor, a CPU, a GPU, an auxiliary processing unit, a FPGA, or the like. In various embodiments, the method 400 is performed by use of a website used for dental consultations between a patient and a dentist. In such embodiments, the consultation may occur via web video conferencing and may use information handling devices 102 of the patient and the dentist. In certain embodiments, the website may enable patients with toothaches, dental related emergencies, general questions, a desire for a second option, and so forth to have a consultation with a dentist without having to travel to a dental office.

The method 400 may include a patient accessing a website and providing 402 intake information. The intake information may be provided on an intake information form. In some embodiments, the intake information may include personal information such as a name, an address, an email address, insurance information, a health history, and/or a description of consultation need. In various embodiments, the method 400 includes uploading 404 dental information that may be converted to digital dental information. The digital dental information may include any suitable dental information such as a tooth photo, an x-ray, a treatment plan, and/or diagnostic data. In certain embodiments, the digital dental information may be uploaded real time using dental machinery. For example, the dental machinery may include a home imaging hardware and/or software used to take pictures of teeth. The method 400 includes, in one embodiment, completing 406 legal information. In various embodiments, the legal information may include a simple legal form with disclosure information.

In certain embodiments, the method 400 includes submitting 408 consultation payment. The consultation payment may be any suitable consultation fee for services. The method 400 may include using hardware and/or software to process a payment made by a patient. In some embodiments, the method 400 includes scheduling 410 an appointment. For example, in response to information being submitted by a patient and the patient submitting a consultation payment, the method 400 may enable the patient to schedule 410 the appointment. The appointment may be scheduled using an online scheduler that may show the patient available dates and/or times for a video conferencing consultation. In certain embodiments, a length of time for the scheduled appointment is established. The length of time for the scheduled appointment may be any suitable length of time, such as 5 minutes, 10 minutes, 15 minutes, 20 minutes, 30 minutes, 60 minutes, and so forth. In various embodiments, the consultation payment may be based on the length of time scheduled for the appointment. In some embodiments, a link to the scheduled appointment may be emailed to the patient. The email may include a link used for video chat.

In various embodiments, the method 400 includes completing 412 the consultation. At the time of the consultation, in some embodiments, a patient may click on their emailed link and connect with a dentist via a video conferencing software. In certain embodiments, a consultation may take place between a patient and a dentist on their respective computers (e.g., information handling devices 102) via web video conferencing. In some embodiments, the consultation may include diagnosis of dental needs performed by the dentist and/or determined by software analysis of information provided by the patient, co-diagnosis of dental needs by dentist and patient, recommendations to buy products for dental needs, general dental education and advice, and/or emailed links provided to the patient that include dental education videos for further dental education. In various embodiments, a conformation of a need and/or a recommendation for an actual visit to a dentist may be made during the online consultation. In certain embodiments, if there are in office dental needs, the method 400 may include scheduling the patient for a dental appointment at a local dental office. In such embodiments, an appointment conformation may be emailed to the patient and treatment may take place at the dental office. In some embodiments, the consultation may include questions about orthodontics, cosmetics, oral surgery, implants, toothaches, restorative treatments, endodontic treatments, emergency care, pediatric questions, and other dental related questions.

In some embodiments, the consultation may include the dentist instructing the patient to attach a mechanical device to the video consultation session. The mechanical device may be controlled remotely by the dentist to aid in diagnosing and/or treating a dental related issue. The mechanical device may be any suitable mechanical device, such as a camera, a cell phone, an x-ray machine, a robotic arm, a mold capturing machine, a 3-dimensional scanning device, and so forth.

In certain embodiments, during a video consultation appointment, a dentist may be able to help and educate a patient through consulting and talking with the patient. In some embodiments, the dentist may provide dental education via dental education modules on a website or via email links sent to the patient to give more extensive education. In various embodiments, as a result of the consultation, the dentist may refer a patient to resources and/or products available to buy at local or online stores via a product line that facilitates treating dental needs. In certain embodiments, a dentist may walk a patent through how to use a product and/or treat a diagnosed issue. In some embodiments, the dentist may assist the patient in using the product by linking the product to a video session and enabling the dentist to control how the product is used remotely via the video session.

In various embodiments, a consultation may enable a dentist to walk a patient through a co-diagnosis of an issue via the patient and the dentist working together. In some embodiments, pharmacy prescriptions may be made as a result of the consultation. In certain embodiments, the patient intake form and photos may be used to assess needs and make a diagnosis for a patient and to determine whether an in-office visit is needed or if a dental need is able to be met with a prescription, consultation, and/or product recommendation.

In some embodiments, a video conference call may be completed as a result of the consultation being performed and/or the problem being addressed. In certain embodiments, a patient may have been helped sufficiently by the video consultation and no further dental treatment or follow up is needed. In various embodiments, a summary of the video consultation may be emailed to a patient for their records and/or stored with the patient's online records.

If it is determined that a patient needs in-office dental treatment as a result of the video conference, then a dentist may schedule an appointment during the video conference for the patient to be seen at a dental office. The dentist may give the patient a confirmed appointment date and/or time for in-office treatment. In some embodiments, an email conformation may be sent to the patient with the in-office appointment date and/or time.

Various products may be recommended to a patient during the video conference. These products may be used for treating canker sores, treating broken teeth, re-cementation of loose crowns, treating periodontal disease, treating denture sores, fixing loose dentures, helping to pull loose baby teeth, and/or pain relief (e.g., via a gel for teeth coming in or problem areas).

As may be appreciated, while features described herein relate to dental video consultations, the methods, systems, and apparatuses described herein may be applied to all dental fields including, but not limited to, orthodontics, oral surgery, endodontics, prosthodontics, periodontics, pedodontics, and other dental specialties. The methods, systems, and apparatuses described herein may also be applied to veterinary medicine, optometry, and other medical fields.

It should be noted that insurance companies may enable patients having their dental insurance to connect with a dentist for a consultation to identify issues and/or give a second opinion to confirm treatment needs before their dental insurance is utilized.

In some embodiments, after a web video conferencing consultation is complete, a patient may have an opportunity to provide a review of a dentist and to provide feedback about how helpful the dental consultation was.

Figure 5:
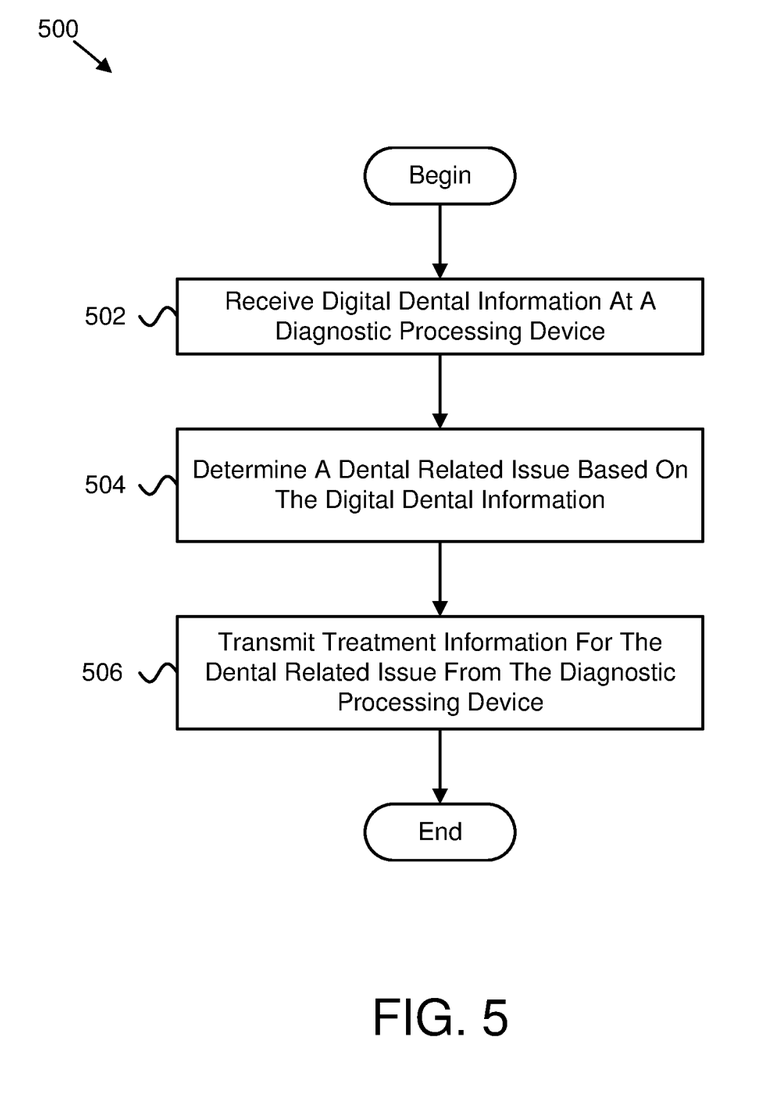
FIG. 5 is a schematic flow chart diagram illustrating another embodiment of a method for remote dentistry.

FIG. 5 is a schematic flow chart diagram illustrating another embodiment of a method 500 for remote dentistry. In some embodiments, the method 500 is performed by an apparatus, such as the information handling device 102. In certain embodiments, the method 500 may be performed by a processor executing program code, for example, a microcontroller, a microprocessor, a CPU, a GPU, an auxiliary processing unit, a FPGA, or the like.

The method 500 may include receiving 502 digital dental information. In various embodiments, the method 500 includes determining 504 a dental related issue based on the digital dental information. The method 500 includes, in one embodiment, transmitting 506 treatment information for the dental related issue from the diagnostic processing device.

In one embodiment, receiving the digital dental information includes receiving an image of a tooth, a face, a mouth, or some combination thereof. In a further embodiment, the image includes an x-ray, a picture, a video, or some combination thereof. In certain embodiments, determining the dental related issue includes digitally analyzing the digital dental information and determining the dental related issue as a result of digitally analyzing the digital dental information. In some embodiments, transmitting the treatment information includes transmitting a prescription. In certain embodiments, transmitting the treatment information includes transmitting instructions to treat the dental related issue. In one embodiment, transmitting the treatment information includes performing the treatment on a patient by verbally instructing the patient on how to perform the treatment. In certain embodiments, transmitting the treatment information includes transmitting the treatment information to a machine that performs the treatment on a patent.

The embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
 an information reception module of artificial intelligence based hardware that:
  receives intake information from a patient;
  receives a completed legal form from the patient, wherein the legal form comprises disclosure information;
  receives payment for consultation services;
  receives scheduling information for scheduling a single video conference call between the patient and a dentist;
  instructs the patient to connect dental machinery to the information reception module during the single video conference call; and
  receives digital dental information comprising a digital conversion of an x-ray, or a picture, or both of a tooth corresponding to the patient, wherein the information reception module comprises the dental machinery, and the dental machinery comprises home imaging hardware used remotely by the dentist to take pictures of teeth, wherein the digital dental information is received during the single video conference call;
 an issue determination module that:
  digitally analyzes the digital conversion of the x-ray, or the picture, or both of the tooth; and
  determines, during the single video conference call between the patient and the dentist, a dental related issue of the patient based solely on the digital analysis of digital conversion of the x-ray, or the picture, or both of the tooth, wherein the dental related issue comprises a toothache, an oral surgery issue, an implant issue, a request for a second opinion, or some combination thereof; and
 a treatment module that transmits treatment information for the toothache, the oral surgery issue, the implant issue, the request for a second opinion, or some combination thereof determined by the issue determination module, wherein transmitting the treatment information comprises transmitting the treatment information to a machine having a robotic arm during the single video conference call between the patient and the dentist, wherein the robotic arm receives and executes the treatment information to perform the treatment of the toothache, the oral surgery issue, the implant issue, or some combination thereof on the patient, and transmitting the treatment information further comprises:
  transmitting instructions to treat the toothache, the oral surgery issue, the implant issue, or some combination thereof;
 wherein at least a portion of the information reception module, the issue determination module, and the treatment module comprises one or more of hardware and executable code, the executable code being stored on one or more computer readable storage media, and operations of the information reception module, the issue determination module, and the treatment module are all performed during the single video conference call between the patient and the dentist.

2. A method at a device, the method comprising:
 receiving, by artificial intelligence based hardware, intake information from a patient;
 receiving, by the artificial intelligence based hardware, a completed legal form from the patient, wherein the legal form comprises disclosure information;
 receiving, by the artificial intelligence based hardware, payment for consultation services;
 receiving, by the artificial intelligence based hardware, scheduling information for scheduling a single video conference call between the patient and a dentist; and
 during the single video conference call, perform all of the following:
  instructing the patient to connect dental machinery to the artificial intelligence based hardware;
  receiving digital dental information comprising a digital conversion of an x-ray, or a picture, or both of a tooth corresponding to the patient, wherein the information reception module comprises the dental machinery, and the dental machinery comprises home imaging hardware used remotely by the dentist to take pictures of teeth, wherein the digital dental information is received during the single video conference call;
  digitally analyzing the digital conversion of the x-ray, or the picture, or both of the tooth;
  determining, during the single video conference call between the patient and the dentist, a dental related issue of the patient based solely on the digital analysis of digital conversion of the x-ray, or the picture, or both of the tooth, wherein the dental related issue comprises a toothache, an oral surgery issue, an implant issue, a request for a second opinion, or some combination thereof; and
  transmitting treatment information for the toothache, the oral surgery issue, the implant issue, the request for a second opinion, or some combination thereof, wherein transmitting the treatment information comprises transmitting the treatment information to a machine having a robotic arm during the single video conference call between the patient and the dentist, wherein the robotic arm receives and executes the treatment information to perform the treatment of the toothache, the oral surgery issue, the implant issue, or some combination thereof on the patient, and transmitting the treatment information further comprises:
   transmitting instructions to treat the toothache, the oral surgery issue, the implant issue, or some combination thereof.

3. A computer program product comprising a non-transitory computer readable storage medium having program instructions embodied therewith, the program instructions executable by a processor to cause the processor to:
 receive, by artificial intelligence based hardware, intake information from a patient;
 receive, by the artificial intelligence based hardware, a completed legal form from the patient, wherein the legal form comprises disclosure information;
 receive, by the artificial intelligence based hardware, payment for consultation services;
 receive, by the artificial intelligence based hardware, scheduling information for scheduling a single video conference call between the patient and a dentist; and
 during the single video conference call, perform all of the following:
  instruct the patient to connect dental machinery to the artificial intelligence based hardware;

receive digital dental information comprising a digital conversion of an x-ray, or a picture, or both of a tooth corresponding to the patient, wherein the information reception module comprises the dental machinery, and the dental machinery comprises home imaging hardware used remotely by the dentist to take pictures of teeth, wherein the digital dental information is received during the single video conference call;

digitally analyze the digital conversion of the x-ray, or the picture, or both of the tooth;

determine, during the single video conference call between the patient and the dentist, a dental related issue of the patient based solely on the digital analysis of digital conversion of the x-ray, or the picture, or both of the tooth, wherein the dental related issue comprises a toothache, an oral surgery issue, an implant issue, a request for a second opinion, or some combination thereof; and transmit treatment information for the toothache, the oral surgery issue, the implant issue, the request for a second opinion, or some combination thereof, wherein transmitting the treatment information comprises transmitting the treatment information to a machine having a robotic arm during the single video conference call between the patient and the dentist, wherein the robotic arm receives and executes the treatment information to perform the treatment of the toothache, the oral surgery issue, the implant issue, or some combination thereof on the patient, and transmitting the treatment information further comprises:

transmitting instructions to treat the toothache, the oral surgery issue, the implant issue, or some combination thereof.

* * * * *